(12) United States Patent
Hu et al.

(10) Patent No.: US 7,544,692 B2
(45) Date of Patent: *Jun. 9, 2009

(54) POLYMORPHIC AND OTHER CRYSTALLINE FORMS OF CIS-FTC

(75) Inventors: Yuerong Hu, West Lafayette, IN (US); Kenneth R. Phares, Chapel Hill, NC (US); Devalina Law, Libertyville, IL (US)

(73) Assignee: Gilead Sciences, Inc., Foster City, CA (US)

( * ) Notice: Subject to any disclaimer, the term of this patent is extended or adjusted under 35 U.S.C. 154(b) by 493 days.

This patent is subject to a terminal disclaimer.

(21) Appl. No.: 10/827,615

(22) Filed: Apr. 19, 2004

(65) Prior Publication Data

US 2005/0026934 A1 Feb. 3, 2005

Related U.S. Application Data

(62) Division of application No. 10/086,830, filed on Mar. 1, 2002, now Pat. No. 6,723,728.

(60) Provisional application No. 60/272,560, filed on Mar. 1, 2001, provisional application No. 60/309,605, filed on Aug. 2, 2001.

(51) Int. Cl.
C07D 411/04 (2006.01)
A61K 31/506 (2006.01)

(52) U.S. Cl. ................... 514/274; 544/317
(58) Field of Classification Search ........ 544/317; 514/274
See application file for complete search history.

(56) References Cited

U.S. PATENT DOCUMENTS

| | | | |
|---|---|---|---|
| 4,476,248 A | 10/1984 | Gordon et al. | |
| 4,522,811 A | 6/1985 | Eppstein et al. | |
| 5,041,449 A | 8/1991 | Belleau et al. | |
| 5,047,407 A | 9/1991 | Belleau et al. | |
| 5,075,445 A | 12/1991 | Jarvest et al. | |
| 5,142,051 A | 8/1992 | Holy et al. | |
| 5,149,794 A | 9/1992 | Yatvin et al. | |
| 5,179,104 A | 1/1993 | Chu et al. | |
| 5,194,654 A | 3/1993 | Hostetler et al. | |
| 5,204,466 A | 4/1993 | Liotta et al. | |
| 5,210,085 A | 5/1993 | Liotta et al. | |
| 5,223,263 A | 6/1993 | Hostetler et al. | |
| 5,234,913 A | 8/1993 | Furman, Jr. et al. | |
| 5,256,641 A | 10/1993 | Yatvin et al. | |
| 5,272,151 A | 12/1993 | Marzi et al. | |
| 5,411,947 A | 5/1995 | Hostetler et al. | |
| 5,444,063 A | 8/1995 | Schinazi | |
| 5,463,092 A | 10/1995 | Hostetler et al. | |
| 5,486,520 A | 1/1996 | Belleau et al. | |
| 5,538,975 A | 7/1996 | Dionne | |
| 5,539,116 A | 7/1996 | Liotta et al. | |
| 5,543,389 A | 8/1996 | Yatvin et al. | |
| 5,543,390 A | 8/1996 | Yatvin et al. | |
| 5,543,391 A | 8/1996 | Yatvin et al. | |
| 5,554,728 A | 9/1996 | Basava et al. | |
| 5,565,438 A | 10/1996 | Chu et al. | |
| 5,567,688 A | 10/1996 | Chu et al. | |
| 5,587,362 A | 12/1996 | Chu et al. | |
| 5,618,820 A | 4/1997 | Dionne | |
| 5,641,763 A | 6/1997 | Holy et al. | |
| 5,663,320 A | 9/1997 | Mansour et al. | |
| 5,674,849 A | 10/1997 | Twist et al. | |
| 5,684,010 A | 11/1997 | Schinazi | |
| 5,684,153 A | 11/1997 | Geen et al. | |
| 5,684,164 A | 11/1997 | Belleau et al. | |
| 5,693,787 A | 12/1997 | Mansour et al. | |
| 5,696,254 A | 12/1997 | Mansour et al. | |
| 5,700,937 A | 12/1997 | Liotta et al. | |
| 5,728,575 A | 3/1998 | Liotta et al. | |
| 5,744,596 A | 4/1998 | Mansour et al. | |
| 5,756,478 A | 5/1998 | Cheng et al. | |

(Continued)

FOREIGN PATENT DOCUMENTS

EP 0 141 927 8/1984

(Continued)

OTHER PUBLICATIONS

Chang, C.-N., et al., "Deoxycytidine deaminase-resistant stereoisomer is the active form of (±)-2',3'-dideoxy-3'-thiacytidine in the inhibition of hepatitis B virus replication," *J. Biol. Chem.*, 267(20):13938-13942 (1992).

(Continued)

*Primary Examiner*—Deepak Rao
(74) *Attorney, Agent, or Firm*—King & Spalding

(57) ABSTRACT

Solid phases of (−)-cis-FTC, which are designated herein as amorphous (−)-FTC and Forms II and III (−)-cis-FTC) are provided that can be distinguished from Form I (−)-cis-FTC by X-ray powder diffraction patterns, thermal properties, and methods of manufacture. A hydrated crystalline form of (±)-cis-FTC (i.e. racemic cis-FTC), and a dehydrated form of the hydrate, are also provided, and can similarly be distinguished from other forms of FTC by X-ray powder diffraction patterns, thermal properties, and methods of manufacture. These FTC forms can be used in the manufacture of other forms of FTC, or in pharmaceutical compositions. Particularly preferred uses of these forms are in the treatment of HIV or hepatitis B.

9 Claims, 15 Drawing Sheets

U.S. PATENT DOCUMENTS

| | | | |
|---|---|---|---|
| 5,756,706 | A | 5/1998 | Mansour et al. |
| 5,763,606 | A | 6/1998 | Mansour et al. |
| 5,767,122 | A | 6/1998 | Chu et al. |
| 5,808,040 | A | 9/1998 | Chu et al. |
| 5,814,639 | A | 9/1998 | Liotta et al. |
| 5,827,727 | A | 10/1998 | Liotta et al. |
| 5,869,461 | A | 2/1999 | Cheng et al. |
| 5,892,025 | A | 4/1999 | Liotta et al. |
| 5,905,082 | A | 5/1999 | Roberts et al. |
| 5,914,331 | A | 6/1999 | Liotta et al. |
| 5,922,867 | A | 7/1999 | Mansour et al. |
| 6,071,922 | A | 6/2000 | Schinazi et al. |
| 6,177,435 | B1 | 1/2001 | Larder et al. |
| 6,228,860 | B1 * | 5/2001 | Mansour et al. ........ 514/263.23 |
| 6,600,044 | B2 * | 7/2003 | Murthy et al. .............. 544/264 |
| 6,642,245 | B1 | 11/2003 | Liotta et al. |
| 6,703,396 | B1 | 3/2004 | Liotta et al. |
| 6,723,728 | B2 | 4/2004 | Hu et al. |

FOREIGN PATENT DOCUMENTS

| | | |
|---|---|---|
| EP | 0 253 412 | 7/1987 |
| EP | 0 337 713 | 4/1989 |
| EP | 0 382 526 | 2/1990 |
| EP | 0 711 771 | 2/1990 |
| EP | 0 513 200 | 1/1991 |
| EP | 0 494 119 | 1/1992 |
| EP | 0 515 144 | 5/1992 |
| EP | 0 517 145 A1 | 6/1992 |
| WO | WO 89/02733 | 9/1988 |
| WO | WO 90/00555 | 1/1990 |
| WO | WO 91/16920 | 4/1991 |
| WO | WO 91/17159 | 5/1991 |
| WO | WO 91/18914 | 5/1991 |
| WO | WO 91/19721 | 6/1991 |
| WO | WO 91/11186 | 8/1991 |
| WO | WO 92/18517 | 4/1992 |
| WO | WO 92/10497 | 6/1992 |
| WO | WO 92/14743 | 9/1992 |
| WO | WO 92/21676 | 12/1992 |
| WO | WO 93/00910 | 1/1993 |
| WO | WO 94/04154 | 3/1994 |
| WO | WO 94/09793 | 5/1994 |
| WO | WO 94/26273 | 11/1994 |
| WO | WO 95/20595 | 1/1995 |
| WO | WO 95/29174 | 4/1995 |
| WO | WO 98/23285 | 6/1998 |
| WO | WO 00/09494 | 2/2000 |
| WO | WO 00/22157 A1 | 4/2000 |
| WO | WO 02/070518 A1 | 9/2002 |

OTHER PUBLICATIONS

Choi, W.-B., et al., "In situ complexation directs the stereochemistry of N-glycosylation in the synthesis of oxathiolanyl and dioxolanyl nucleoside analogues," *J. Am. Chem. Soc.*, 113(24):9377-9379 (1991).

DaVisson, V.J., et al., "Synthesis of Nucleotide 5'-Diphosphates from 5'-O-Tosyl Nucleosides," *J. Org. Chem.*, 52(9):1794-1801 (1987).

Furman, P.A., et al., "The Anti-Hepatitis B Virus Activities, Cytotoxicities, and Anabolic Profiles of the (−) and (+) Enantiomers of cis-5-Fluoro-1-[2-(Hydroxymethyl)-1,3-oxathiolane-5-yl]-Cytosine" *Antimicrobial Agents and Chemotherapy*, 36(12):2686-2692 (Dec. 1992).

Hoard, D.E., et al., "Conversion of Mono- and Oligodeoxyribonucleotides to 5'-Triphosphates," *J. Am. Chem. Soc.*, 87(8):1785-1788 (Apr. 20, 1965).

Imai, K., et al., "Studies on Phosphorylation. IV. Selective Phosphorylation of the Primary Hydroxyl Group in Nucleosides." *J. Org. Chem.*, 34(6):1547-1550 (Jun. 1969).

International Search Report for WO02/070518, dated Jul. 23, 2002.

Jones, R.J., et al., "Mini Review: Nucleotide prodrugs," *Antiviral Research*, 27:1-17 (1995).

Jozwiakowski, M.J., et al., "Solubility Behavior of Lamivudine Crystal Forms in Recrystallization Solvents", *J. Pharm. Sci.*, 85(2):193-199 (1996).

Korba et al., "Penciclovir is a Selective Inhibitor of Hepatitis B Virus Replication in cultured Human Hepatoblastoma Cells," *Antimicrobial Agents and Chemotherapy*, Abstract (1996).

Korba et al.; "Use of a Standardized Cell Culture Assay to Assess Activities of Nucleoside Analogs Angainst Hepatitis B Virus Replication," *Antiviral Research*, (1992):55-70.

Korba, Brent E., "In Vitro Evaluation of Combination Therapies Against Hepatitis B Virus Replication," *Antiviral Research*, (1995):49-51.

Kruger et al.. "Treatment of Hepatitis B-related Polyarteritis Nodosa with Famciclovir and Interferon Alfa-2b," *Journal of Hepatology*, Abstract (1997).

Migyoung et al.; "Dioxolane Cytosine Nucleosides as Anti-Hepatitis B Agents," *Bioorganic & Medicinal Chemistry Letters*; 5(17):2011-2014 (1995).

Norbeck, D. W. et al., "A new 2',3'-dideoxynucleoside prototype with in vitro activity against HIV," *Tetrahedron Letters*, 30(46):6263-6266 (1989).

Schinazi, R.F., et al., "Selective Inhibition of Human Immunodeficiency Viruses by Racemates and Enantiomers of cis-5-Fluoro-1-[2-(Hydroxymethyl)-1,3-Oxathiolane-5-yl] Cytosine," *Antimicrobial Agents and Chemotherapy*, 36(11):2423-2431 (Nov. 1992).

Von Janta-Lipinski, M., et al., "Newly Synthesized L-Enantiomers of 3'-Fluoro-Modified β-2'-Deoxyribonucleoside 5'-Triphosphates Inhibit Hepatitis B DNA Polymerase but not the Five Cellular DNA Polymerases α, β, γ, δ, and ε Nor HIV-1 Reverse Transcriptase," *J. Med. Chem.*, 41(12):2040-2046 (May 21, 1998).

* cited by examiner

POLYMORPHIC AND OTHER CRYSTALLINE FORMS OF CIS-FTC

RELATED APPLICATIONS

This application is a division of U.S. patent application Ser. No. 10/086,830, filed Mar. 1, 2002, now U.S. Pat. No. 6,723,728, which claims priority to U.S. Provisional Application No. 60/272,560, filed Mar. 1, 2001, and U.S. Provisional Application No. 60/309,605, filed Aug. 2, 2001.

FIELD OF THE INVENTION

The present invention relates to polymorphic and other crystalline forms of (−)- and (±)-cis-FTC (4-amino-5-fluoro-1-(2-(hydroxymethyl)-1,3-oxathiolan-5-yl)-2(1H)-pyrimidinone), pharmaceutical compositions thereof, and uses for such compositions.

BACKGROUND OF THE INVENTION

The success of various synthetic nucleosides such as AZT, D4T, DDI, and DDC in inhibiting the replication of HIV in vivo or in vitro led researchers in the late 1980's to design and test nucleosides that substitute a heteroatom for the carbon atom at the 3'-position of the nucleoside. Norbeck, et al., disclosed that (±)-1-[cis-(2,4)-2-(hydroxymethyl)-4-dioxolanyl]thymine (referred to as (±)-dioxolane-T) exhibits a modest activity against HIV ($EC_{50}$ of 20 uM in ATH8 cells), and is not toxic to uninfected control cells at a concentration of 200 uM. *Tetrahedron Letters* 30 (46), 6246, (1989). European Patent Application Publication No. 337 713 and U.S. Pat. No. 5,041,449, assigned to BioChem Pharma, Inc., disclose racemic 2-substituted-4-substituted-1,3-dioxolanes that exhibit antiviral activity. Published PCT application numbers PCT US91/09124 and PCT US93/08044 disclose isolated β-D-1,3-dioxolanyl nucleosides for the treatment of HIV infection. WO 94/09793 discloses the use of isolated β-D-1,3-dioxolanyl nucleosides for the treatment of HBV infection.

U.S. Pat. No. 5,047,407 and European Patent Application Publication No. 0 382 526, also assigned to BioChem Pharma, Inc., disclose that a number of racemic 2-substituted-5-substituted-1,3-oxathiolane nucleosides have antiviral activity, and specifically report that the racemic mixture of 2-hydroxymethyl-5-(cytosin-1-yl)-1,3-oxathiolane (referred to below as BCH-189) has approximately the same activity against HIV as AZT, with less toxicity. The (−)-enantiomer of BCH-189 (U.S. Pat. No. 5,539,116 to Liotta, et al.), known as 3TC, is now sold commercially for the treatment of HIV in humans in the United States. See also EP 513 200 B1.

It has also been disclosed that (−)-(cis)-FTC (4-amino-5-fluoro-1-(2-(hydroxymethyl)-1,3-oxathiolan-5-yl)-2(1H)-pyrimidinone (2R-cis), or β-L-2-hydroxymethyl-5-(5-fluorocytosin-1-yl)-1,3-oxathiolane) has potent HIV activity. See Schinazi, et al., "Selective Inhibition of Human Immunodeficiency viruses by Racemates and Enantiomers of cis-5-Fluoro-1-[2-(Hydroxymethyl)-1,3-Oxathiolane-5-yl]Cytosine" *Antimicrobial Agents and Chemotherapy*, November 1992, page 2423-2431. See also U.S. Pat. Nos. 5,814,639; 5,914,331; 5,210,085; U.S. Pat. No. 5,204,466, WO 91/11186, and WO 92/14743. The chemical structure of (−)-cis-FTC is shown below:

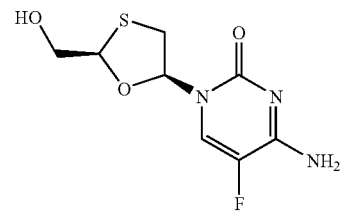

$C_8H_{10}FN_3O_3s$
Mol. Wt.: 247.25

Because of the commercial importance of 1,3-oxathiolane nucleosides such as FTC, a number of processes for their production have been described in patents and scientific literature. The substituents on the chiral carbons (the specified purine or pyrimidine base (referred to as the C5 substituent)) and $CH_2OH$ (referred to as the C2 substituent)) of 1,3-oxathiolane nucleosides can be either cis (on the same side) or trans (on opposite sides) with respect to the oxathiolane ring system. Both the cis and trans racemates consist of a pair of optical isomers. Hence, each compound has four individual optical isomers. The four optical isomers are represented by the following configurations (when orienting the oxathiolane moiety in a horizontal plane such that the —S—$CH_2$— moiety is in back): (1) cis (also referred to as β), with both groups "up", which is the naturally occurring L-cis configuration (2) cis, with both groups "down", which is the non-naturally occurring β-cis configuration; (3) trans (also referred to as the α-configuration) with the C2 substituent "up" and the C5 substituent "down"; and (4) trans with the C2 substituent "down" and the C5 substituent "up". The two cis enantiomers together are referred to as a racemic mixture of β-enantiomers, and the two trans enantiomers are referred to as a racemic mixture of α-enantiomers. In general, it is fairly standard to be able to separate the pair of cis racemic optical isomers from the pair of trans racemic optical isomers. It is a significantly more difficult challenge to separate or otherwise obtain the individual enantiomers of the cis-configuration. For 3TC and FTC, the desired stereochemical configuration is the P-L-isomer.

The numbering scheme for the 1,3-oxathiolane ring in FTC is given below.

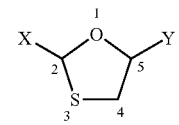

Routes to condense the 1,3-oxathiolane ring with a protected base

U.S. Pat. No. 5,204,466 discloses a method to condense a 1,3-oxathiolane with a protected pyrimidine base using tin chloride as a Lewis acid, which provides virtually complete β-stereoselectivity. See also Choi, et al, "In Situ Complexation Directs the Stereochemistry of N-Glycosylation in the synthesis of Oxathiolanyl and Dioxolanyl Nucleoside Analogues," *J. Am Chem. Soc.* 1991, 213, 9377-9379. The use of tin chloride creates undesirable residues and side products during the reaction which are difficult to remove.

A number of U.S. patents disclose a process for the preparation of 1,3-oxathiolane nucleosides via the condensation of a 1,3-oxathiolane intermediate that has a chiral ester at the 2-position of the ring, with a protected base in the presence of a silicon-based Lewis acid. The ester at the 2-position must then be reduced to the corresponding hydroxymethyl group to afford the final product. See U.S. Pat. Nos. 5,663,320; 5,864, 164; 5,693,787; 5,696,254; 5,744,596; and 5,756,706.

U.S. Pat. No. 5,763,606 discloses a process for producing predominantly cis-2-carboxylic or thiocarboxylic acid 1,3-oxathiolane nucleosides that includes coupling a desired, previously silylated purine or pyrimidine base with a bicyclic intermediate in the presence of a Lewis acid. U.S. Pat. No. 5,272,151 describes a process for the preparation of 1,3-dioxolane nucleosides that includes reacting a 2-O-protected-5-O-acylated-1,3-dioxolane with an oxygen- or nitrogen-protected purine or pyrimidine base in the presence of a titanium catalyst.

Choi, et al, "In Situ Complexation Directs the Stereochemistry of N-Glycosylation in the synthesis of Oxathiolanyl and Dioxolanyl Nucleoside Analogues," *J. Am Chem. Soc.* 1991, 213, 9377-9379, reported that no coupling of the 1,3-oxathiolane with protected pyrimidine base occurs with $HgCl_2$, $Et_2AlCl$, or $TiCl_2(O\text{-isopropyl})_2$ (see footnote 2). Choi also reported that the reaction between anomeric 1,3-oxathiolane acetates with silylated cytosine and virtually any common Lewis acid other than tin chloride resulted in the formation of inseparable mixtures of N-glycosylated anomers.

U.S. Pat. No. 5,922,867 discloses a method for preparing a dioxolane nucleoside that includes glycosylating a purine or pyrimidine base with a 2-protected-oxymethyl-4-halo-1,3-dioxolane.

U.S. Pat. Nos. 5,914,331, 5,700,937, 5,827,727, and 5,892, 025, among others, to Liotta et al. describe coupling the 1,3-oxathiolanes disclosed therein with silyated 5-fluorocytosine in the presence of $SnCl_4$ to form the β(−)isomer of FTC; and optionally removing the protecting groups.

Routes to Provide the 1,3-oxathiolane Nucleoside in the Desired Stereoconfiguration Specific methods for preparing FTC in the desired stereoconfiguration in a substantially pure form are described in U.S. Pat. Nos. 5,914,331, 5,700,937, 5,827,727, and 5,892, 025, among others, to Liotta et al. In one embodiment, the C5'-hydroxyl group of a mixture of nucleoside racemates is reacted with an acyl compound to form C5'-esters in which the nucleoside is in the "carbinol" end of the ester. The desired enantiomer can be isolated by treatment of the racemic mixture with an enzyme that hydrolyses the desired enantiomer (followed by extraction of the polar hydrolysate with a polar solvent) or by treatment with an enzyme that hydrolyses the undesired enantiomer (followed by removal of the undesired enantiomer with a polar solvent). Enzymes that catalyze the hydrolysis of 1,3-oxathiolane pyrimidine nucleosides include pig liver esterase, porcine pancreatic lipase, Amano PS-800 lipase, substillisin, and α-chymotrypsin.

Cytidine-deoxycytidine deaminase can be used to resolve racemic mixtures of 2-hydroxymethyl-5-(cytosin-1-yl)-1,3-oxathiolane and its derivatives, including 2-hydroxymethyl-5-(5-fluoro-cytosin-1-yl)-1,3-oxathiolane. The enzyme catalyses the deamination of the cytosine moiety to a uridine. One of the enantiomers of 1,3-oxathiolane nucleosides is a preferred substrate for cytidine-deoxycytidine deaminase. The enantiomer that is not converted to a uridine (and therefore is still basic) is extracted from solution with an acidic solution. Cytidine-deoxycytidine deaminase can be isolated from rat liver or human liver, or expressed from recombinant sequences in a procaryotic system such as *E. coli*.

Chiral chromatography can also be used to resolve cis-FTC enantiomers. For example, U.S. Pat. No. 5,892,025 to Liotta, et al. discloses a method for resolving a combination of the enantiomers of cis-FTC by passing the cis-FTC through an acetylated β-cyclodextrin chiral column.

Polymorphic Characterization

The ability of a compound to exist in different crystal structures is known as polymorphism. These different crystalline forms are known as "polymorphic modifications" or "polymorphs." While polymorphs have the same chemical composition, they differ in packing and geometrical arrangement, and exhibit different physical properties such as melting point, shape, color, density, hardness, deformability, stability, dissolution, and the like. Depending on their temperature-stability relationship, two polymorphs may be either monotropic or enantiotropic. For a monotropic system, the relative stability between the two solid phases remains unchanged as the temperature is changed. In contrast, in an enantiotropic system there exists a transition temperature at which the stability of the two phases reverse. (Theory and Origin of Polymorphism in "Polymorphism in Pharmaceutical Solids" (1999) ISBN:)-8247-0237).

A number of compounds have been reported to exhibit polymorphism. As an early example; Gordon, et al. in U.S. Pat. No. 4,476,248, disclosed and claimed a new crystalline form of the drug ibuprofen as well as a process for producing it. The new crystalline form was reported to improve the manufacturability of ibuprofen. A structure more closely related to FTC, 3TC ((−)-cis-4-amino-1-(2-hydroxymethyl-1,3-oxathiolan-5-yl)-(1H)-pyrimidine-2-one; lamivudine), is also reported to exist in more than one crystalline form. Jozwiakowski, M. J., Nguyen, N. T., Sisco, J. M., Spancake, C. W. "Solubility Behavior of Lamivudine Crystal Forms in Recrystallization Solvents", *J. Pharm. Sci.*, 85, 2, p.193-199 (1996). See also U.S. Pat. No. 5,905,082 to Roberts et al., entitled "Crystalline Oxathiolane Derivatives," issued May 18, 1999, and its PCT counterpart PCT/EP92/01213, describing two polymorphic forms of 3TC. Roberts et al. disclose that one polymorph is obtained when 3TC is crystallized from an aqueous solution. A second polymorph is obtained when 3TC is crystallized from non-aqueous media, or when the first form is melted and allowed to cool, or when the first form is ground or milled. Both polymorphic forms display-unique absorption bands, melting temperatures, and crystal energies.

(−)-cis-FTC produced by the above described methods has a distinct crystalline form, referred to herein as Form I (−)-cis-FTC. The angular positions (two theta) of the characteristic peaks in a powder X-ray diffraction pattern of (−) cis Form I FTC, shown in FIG. 7, are: 14.1°±0.1°, 19.9°±0.1°, 20.2°±0.1°, 20.6°±0.1°, 21.0°±0.1°, 22.4°±0.1°, 28.5°+0.1°, 29.5°±0.1°, and 32.6°±0.1°.

Additional polymorphs and other crystalline forms of FTC could have commercial value in manufacturing or other applications. It is therefore an objective of this invention to provide novel polymorphic and other crystalline forms of FTC.

It is another objective to provide novel methods for the preparation and isolation of polymorphic and other crystalline forms of FTC.

It is still another objective of the invention to provide therapeutic uses of FTC polymorphs and other phases of FTC.

SUMMARY OF THE INVENTION

Solid phases of (−)-cis-FTC, which are designated herein as amorphous (−)-FTC and Forms II and III (−)-cis-FTC) are provided that can be distinguished from Form I (−)-cis-FTC by X-ray powder diffraction patterns, thermal properties, and methods of manufacture. A hydrated crystalline form of (±)-cis-FTC (i.e. racemic cis-FTC), and a dehydrated form of the hydrate, are also provided, and can similarly be distinguished from other forms of cis-FTC by X-ray powder diffraction patterns, thermal properties, and methods of manufacture. These FTC forms can be used in the manufacture of other forms of FTC, or in pharmaceutical compositions. Particularly preferred uses of these forms are in the treatment of HIV or hepatitis B.

Form II (−)-cis-FTC can be obtained by melting Form I (−)-cis-FTC and allowing the melt to recrystallize at a temperature close to the melting point of Form I. Form III (−)-cis-FTC can be obtained by cooling Form II (−)-cis-FTC below the thermodynamic transition temperature for forms II and III. Amorphous (−)-cis-FTC can be obtained by rapidly cooling liquid (−)-cis-FTC. The hydrated crystalline form of (±)-cis-FTC is a sesquihydrate, and may be obtained by dissolving (±)-cis-FTC in water and recrystallizing the FTC. The dehydrated form of the sesquihydrate can be obtained by removing the waters of hydration from the sesquihydrate.

DETAILED DESCRIPTION OF THE INVENTION

Two new polymorphic forms of (−)-cis-FTC, the amorphous phase of (−)-cis-FTC, one new hydrated crystalline form of (±)-cis-FTC, and a dehydrated form of the (±)-cis-FTC hydrate are provided that can be distinguished from other phases of (−)-cis-FTC and (±)-cis-FTC by X-ray diffraction patterns, thermal properties, and the methods by which they are made. These forms of FTC along with the amorphous phase can be used as intermediates in the manufacture of FTC, or can be formulated into pharmaceutical compositions and used for the treatment of HIV or hepatitis B.

Figure 7:
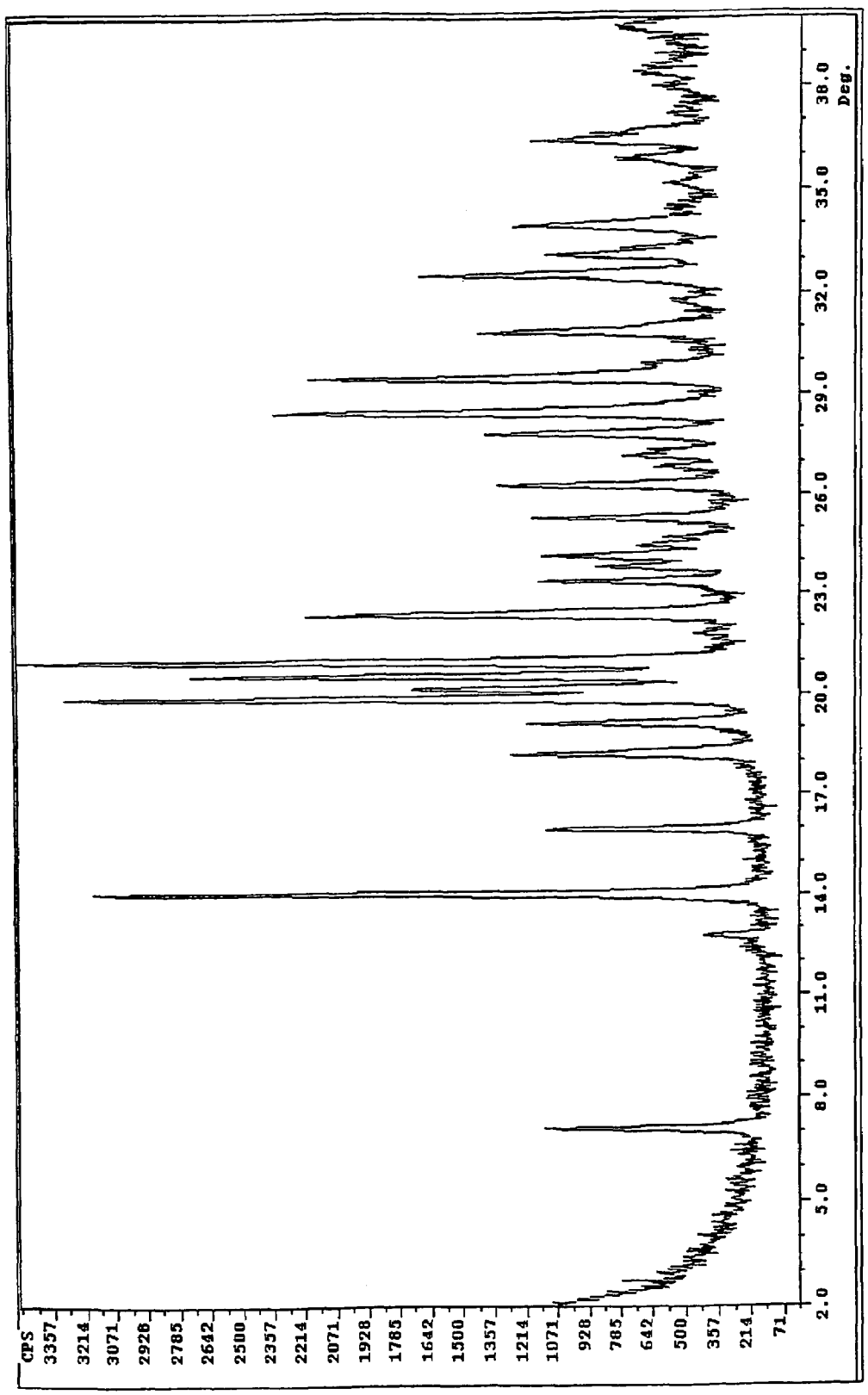
FIG. 7 is a PXRD ("powder X-ray diffraction") pattern of Form I (−)-cis-FTC.
Figure 8:
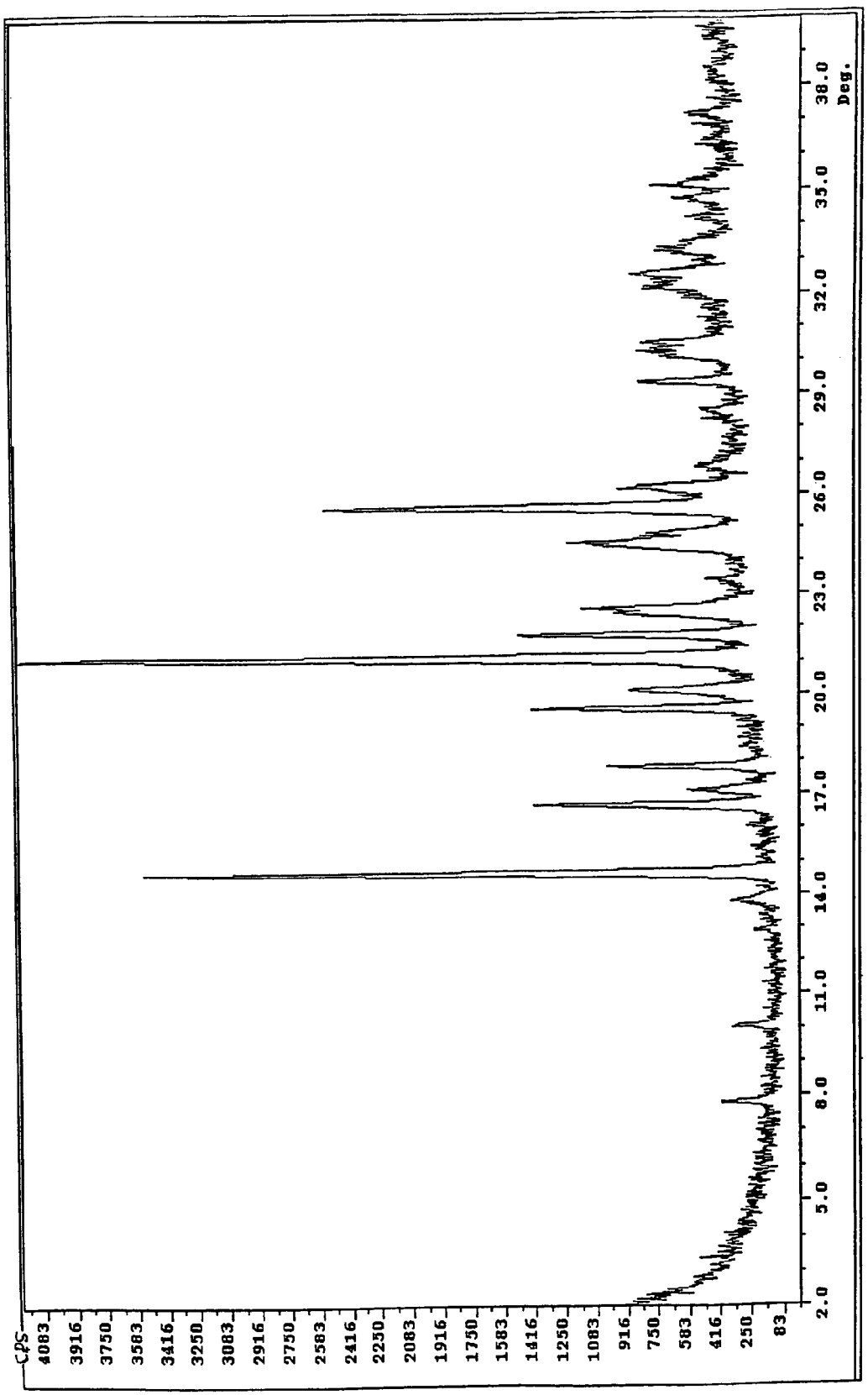
FIG. 8 is a PXRD pattern of Form II (−)-cis-FTC.
Figure 9:
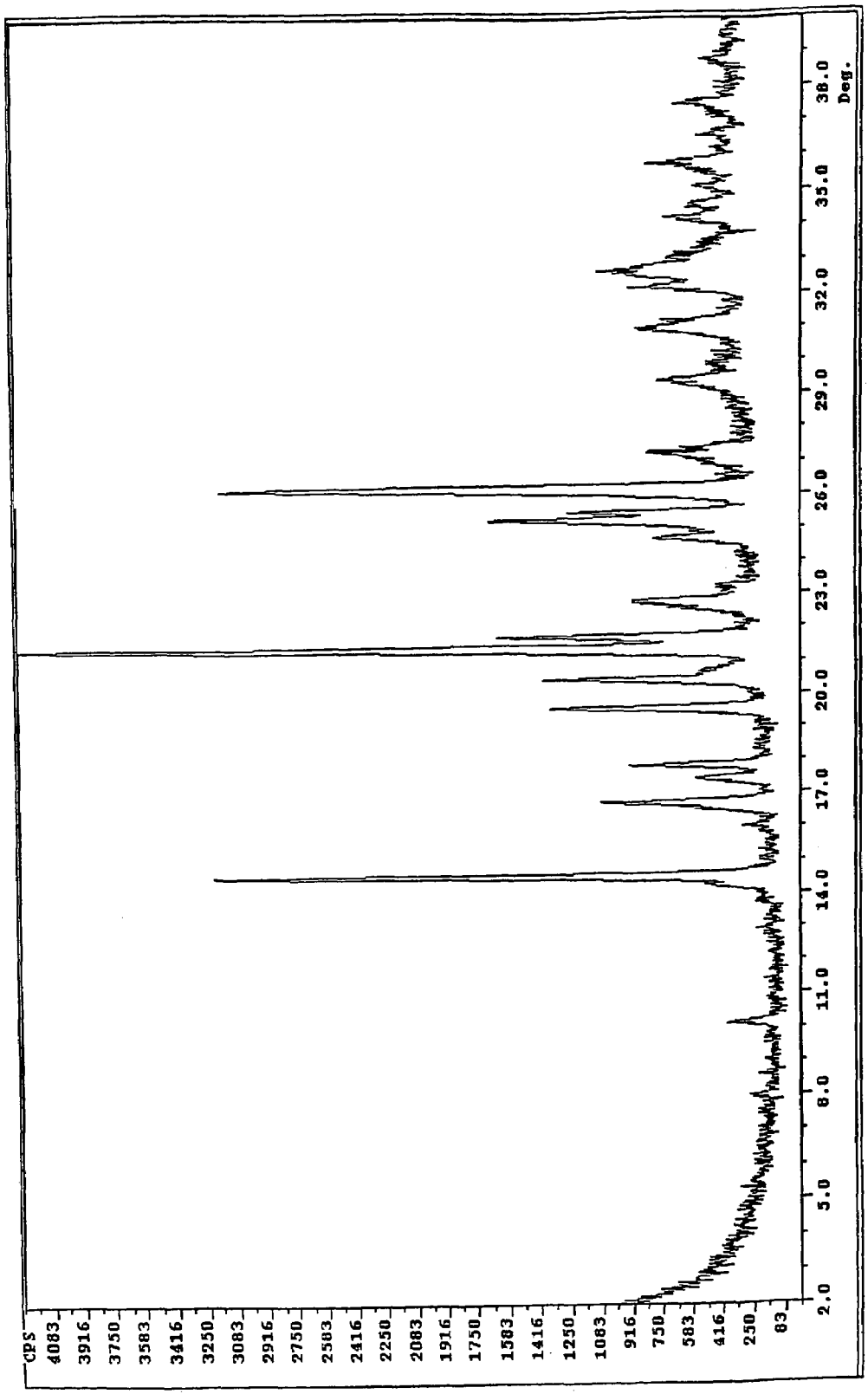
FIG. 9 is a PXRD pattern of Form ImI (−)-cis-FTC.

The two polymorphic forms of (−)-cis-FTC of this invention are designated Forms II and III (−)-cis-FTC, and are characterized by the X-ray powder diffraction patterns in FIGS. 8 and 9. These forms should be contrasted with Form I (−)-cis-FTC, which is the polymorphic form of (−)-cis-FTC prepared by the methods described in the background section of this document. Form I (−)-cis-FTC can be characterized by the X-ray powder diffraction pattern shown in FIG. 7, or by the peaks at the diffraction angles given in the background section of this document.

Figure 10:
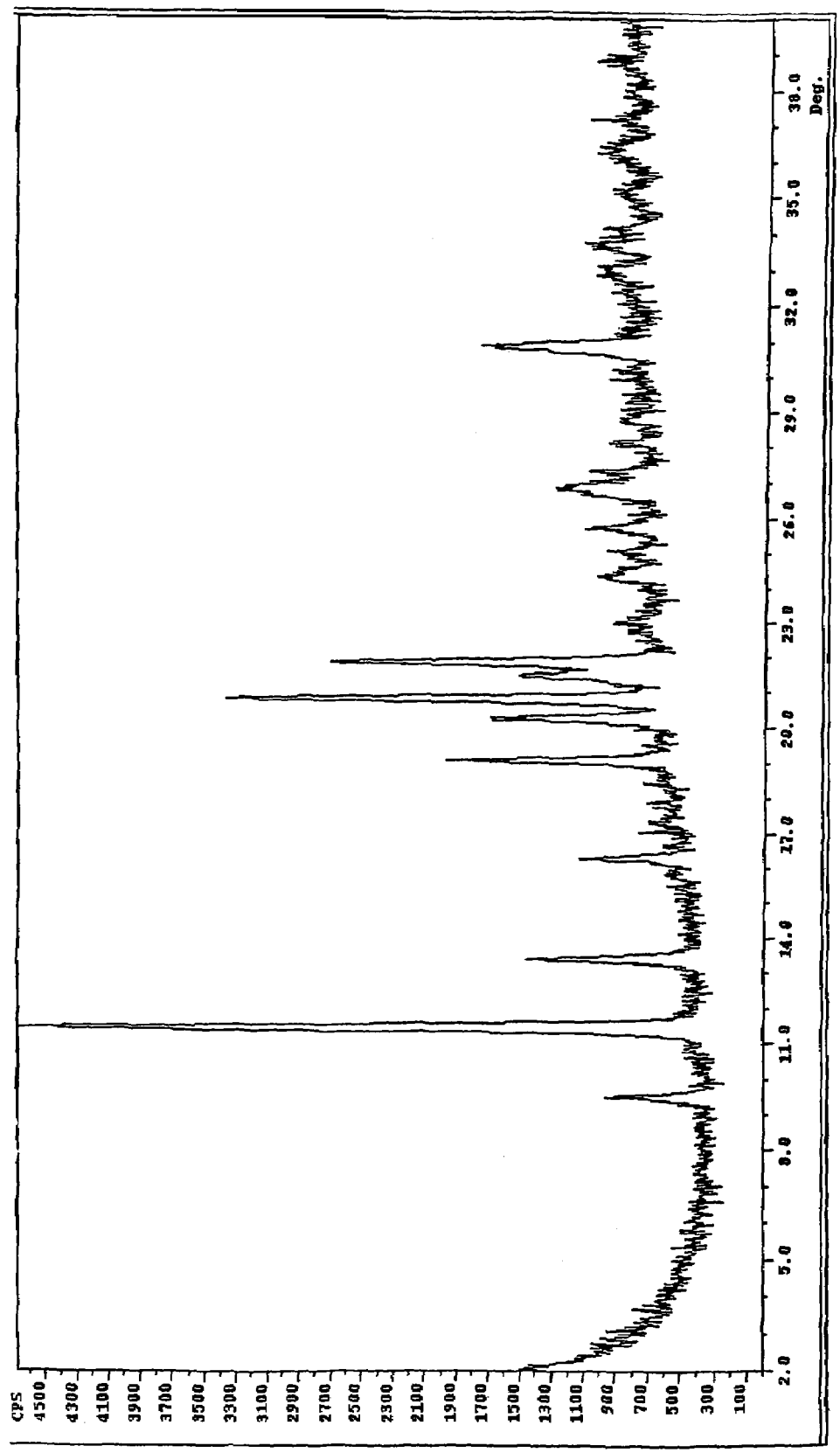
FIG. 10 is a PXRD pattern of the sesquihydrate of (±)-cis-FTC.

The hydrated crystalline form of (±)-cis-FTC is characterized by the X-ray powder diffraction patterns in FIG. 10. This form should be contrasted with the (±)-cis-FTC manufactured in the prior art. The thermal properties for the various forms are summarized in the table below:

| Type of transition $T_{transition}^{phase}$ | Approximate temperature (° C.) | Temperature Range (° C.) |
|---|---|---|
| $T_m^{I}$ | 151 | 148-153 |
| $T_m^{II}$ | 166 | 162-167 |
| $T_m^{III}$ | Not observed in this investigation | Not observed |
| $T_g^{Amorphous}$ | 67 | +/− 3° C. at 10° C./min heating rate |
| $T_t^{I,II}$ | 130 (calculated) | N/A |
| $T_t^{II,III}$ | 102 | 96-112 |
| $T_d^{hydrate}$ | >30 | — |
| $T_m^{racemate}$ | 190 | 185-192 |

Thus, the invention provides:
a) two polymorphs and an amorphous phase of (−)-cis-FTC, as characterized by X-ray powder diffraction analysis, physical properties, and methods of manufacture;
b) a hydrated crystalline form of (±)-cis-FTC, and dehydrated form of the (±)-cis-FTC hydrate, as characterized by X-ray powder diffraction analysis, physical properties, and methods of manufacture;
c) processes for making the (−)-cis-FTC phases and the (±)-cis-FTC crystalline forms;
d) therapeutic and/or pharmaceutical compositions of the (−)-cis-FTC phases and (±)-cis-FTC crystalline forms, optionally in the presence of a pharmaceutically acceptable carrier; and
e) novel therapeutic uses for the (−)-cis-FTC phases and the (+)-cis-FTC crystalline forms, especially in the treatment of viral diseases such as HIV and hepatitis B.

Form II (−)-cis-FTC

Form II (−)-cis-FTC is observed when Form I (−)-cis-FTC is melted and allowed to recrystallize. Like all polymorphs, Form II can be characterized by the powder diffraction pattern it exhibits when subjected to powder X-ray crystallography. The angular positions (two theta) of the characteristic peaks in the powder X-ray diffraction pattern of Form II (−)-cis-FTC, shown in FIG. 8, are: 14.7°±0.1°, 16.7°±0.1°, 19.6°±0.1°, 21.1°±0.1°, 21.8°±0.1°, 24.6°±0.1°, and 25.6°±0.1°.

Form II (−)-cis-FTC can also be characterized by its melting temperature and/or heat of fusion. Form II (−)-cis-FTC has a melting temperature of about 166° C. at atmospheric pressure, and typically exhibits heat of fusion in the range of about 15-19 kJ/mol. It is known that heat of fusion can vary depending on experimental conditions.

Alternatively, Form II (−)-cis-FTC can be characterized by its enantiotropic behavior and the method by which it is manufactured. Form II (−)-cis-FTC is enantiotropic with Form I and Form III polymorphs of (−)-cis-FTC, in the sense that a transition temperature exists below and above which the stability order is reversed. Due to this enantiotropic behavior, Form II (−)-cis-FTC may be prepared from either Form I (−)-cis-FTC or Form III (−)-cis-FTC. In the examples presented in this document, Form II (−)-cis-FTC was obtained:

(1) By heating (−)-cis-FTC (Form I) to above its melting temperature (about 151° C. for Form I), and holding it at that elevated temperature. Upon slow cooling, the melted (−)-cis-FTC recrystallized to Form II, and assumed the crystalline form of Form II, at temperatures greater than the thermodynamic transition temperature between Forms II and III.

(2) By heating Form III (−)-cis-FTC to above the thermodynamic transition temperature for Forms II and III, which ranges from about 96° C. to about 112° C. (because Form II is enantiotropic with Form III (−)-cis-FTC).

Thus, one can obtain Form II (−)-cis-FTC when Form I (−)-cis-FTC is melted and the temperature of the melt is maintained below the melting temperature of Form II but greater than the thermodynamic transition temperature between Forms II and III. Notably, a similar transition from Form II is not observed when Form II is heated to above its melting point (about 166° C.) and allowed to slowly cool. Rather, Form II simply recrystallizes to Form II. However, Form II would not crystallize from the same melt if it was quench cooled; rather, an amorphous phase would result.

Therefore, in one embodiment the invention provides Form II (−)-cis-FTC, preferably in substantially pure form, as characterized by any of the foregoing methods. In another embodiment the invention provides Form II (−)-cis-FTC substantially in the absence of Form I (−)-cis-FTC. In still another embodiment the invention provides Form II (−)-cis-FTC substantially in the absence of Form III (−)-cis-FTC. In yet another embodiment the invention provides a pharmaceutical composition that comprises Form II (−)-cis-FTC, further comprising a pharmaceutically acceptable carrier.

Form III (−)-cis-FTC

Because Form II (−)-cis-FTC undergoes a solid state transition to Form HI (−)-cis-FTC, this form is obtained from Form II (−)-cis-FTC when the temperature of Form II (−)-cis-FTC is dropped below the transition temperature, which ranges from about 96° C. to about 112° C. Form III (−)-cis-FTC is another polymorph of (−)-cis-FTC, and can be characterized by the powder diffraction pattern it exhibits when subjected to powder X-ray crystallography. The angular positions (two theta) of the characteristic peaks in the powder X-ray diffraction pattern of Form III (−)-cis-FTC, shown in FIG. 9, are: 14.5°±0.1°, 16.7°±0.1°, 19.6°±0.1°, 20.4°±0.1°, 21.4°±0.1°, 21.7°±0.1°, 25.2°±0.1°, and 26.2°±0.1°.

Form III (−)-cis-FTC can also be characterized by the methods of its manufacture. Because of Form III's enantiotropic behavior with Form II, Form III (−)-cis-FTC can be prepared from Form II (−)-cis-FTC by cooling Form II (−)-cis-FTC below the solid-state transition temperature for Forms II and Im, and thereby causing a solid state transition from Form II (−)-cis-FTC. Of course, Form III (−)-cis-FTC can also be prepared directly from Form I (−)-cis-FTC, with Form II as an intermediate, by melting Form I and slowly cooling the melt to below the solid-state transition temperature for Forms II and III. Because of this stability below its solid state transition temperature, Form III (−)-cis-FTC can also be characterized by the range of temperatures over which it exhibits a solid state transition, but is preferably characterized at the lower end of this range (i.e. about 96° C. at atmospheric pressure).

Therefore, in one embodiment the invention provides Form III (−)-cis-FTC, preferably in substantially pure form. In another embodiment the invention provides Form III (−)-cis-FTC substantially in the absence of Form I (−)-cis-FTC. In another embodiment the invention provides Form III (−)-cis-FTC substantially in the absence of Form II (−)-cis-FTC. In yet another embodiment the invention provides a pharmaceutical composition that comprises Form III (−)-cis-FTC, further comprising a pharmaceutically acceptable carrier.

(±)-cis-FTC Sesquihydrate (±)-cis-FTC sesquihydrate is a crystalline form of racemic cis-FTC that is obtained when (+)-cis-FTC is dissolved in water and recrystallized. Notably, the hydrate only results from the racemate of cis-FTC, and does not result from pure (−)-cis-FTC. The (±)-cis-FTC sesquihydrate can be characterized by the powder diffraction pattern it exhibits when subjected to powder X-ray crystallography. The angular positions (two theta) of the characteristic peaks in the powder X-ray diffraction pattern of (±)-cis-FTC sesquihydrate, shown in FIG. 10, are: 11.5°±0.1°, 13.4°±0.1°, 19.1°±0.1°, 20.3°±0.1°, 20.8°±0.1°, 21.5°±0.1°, 21.9°±0.1°, and 30.9°±0.1°.

The TGA analyses confirm a sesquihydrate of (+)-cis-FTC. The sesquihydrate begins to lose its water of hydration to evaporation at about 30° C. at atmospheric pressure.

(±)-cis-FTC sesquihydrate can also be characterized by one of the methods for its preparation. (±)-cis-FTC sesquihydrate is preferably prepared simply by dissolving (±)-cis FTC in water, and recrystallizing the dissolved FTC to a hydrated crystalline form. Heat can be employed during dissolution to increase the amount of FTC that is dissolved. The (±)-FTC can be present in a pure racemic mixture of cis-FTC, or as an impurity to a composition that comprises mostly (+)-cis-FTC or (−)-cis-FTC. When present as an impurity, (±)-FTC preferably comprises at least about 4% by weight of the (+)-cis-FTC or (−)-cis-FTC composition (i.e. if present as an impurity of (−)-cis-FTC, the FTC preferably comprises at least 2% of the (+) enantiomer by weight, and if present as an impurity of (+)-cis-FTC, the FTC preferably comprises at least 2% of the (−) enantiomer by weight).

Figure 12:
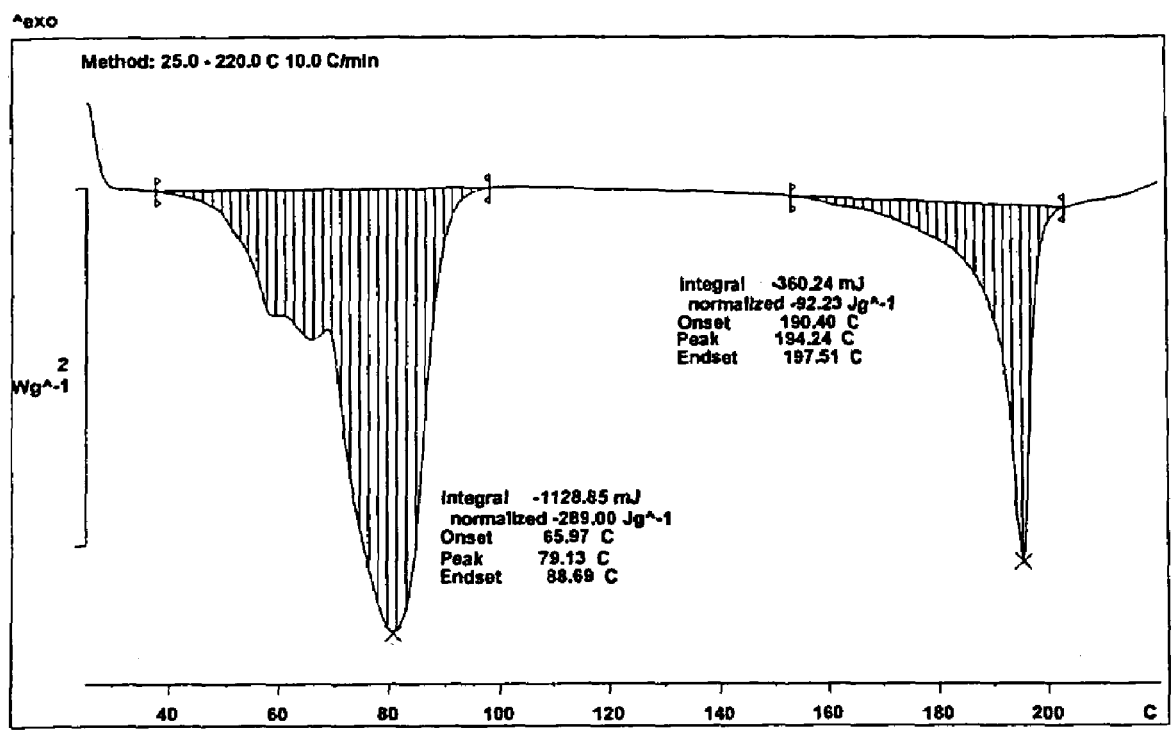
FIG. 12 is a DSC thermogram of (±)-cis-FTC sesquihydrate and (−)-cis-FTC.

A DSC thermogram of (±)-cis-FTC is shown in FIG. 12. The recrystallized FTC is a sesquihydrate, as shown by DSC, TGA, and PXRD analysis.

Therefore, in one embodiment, the invention provides (±)-cis-FTC sesquihydrate, preferably in substantially pure form. In still other embodiments, the invention provides (±)-cis-FTC sesquihydrate substantially in the absence of Form I (−)-cis-FTC, or substantially in the absence of other hydrated and dehydrated crystalline forms of racemic cis-FTC, (−)-cis-FTC, or (+)-cis-FTC. In still another embodiment the invention provides a pharmaceutical composition that comprises (±)-cis-FTC sesquihydrate, further comprising a pharmaceutically acceptable carrier.

Figure 11:
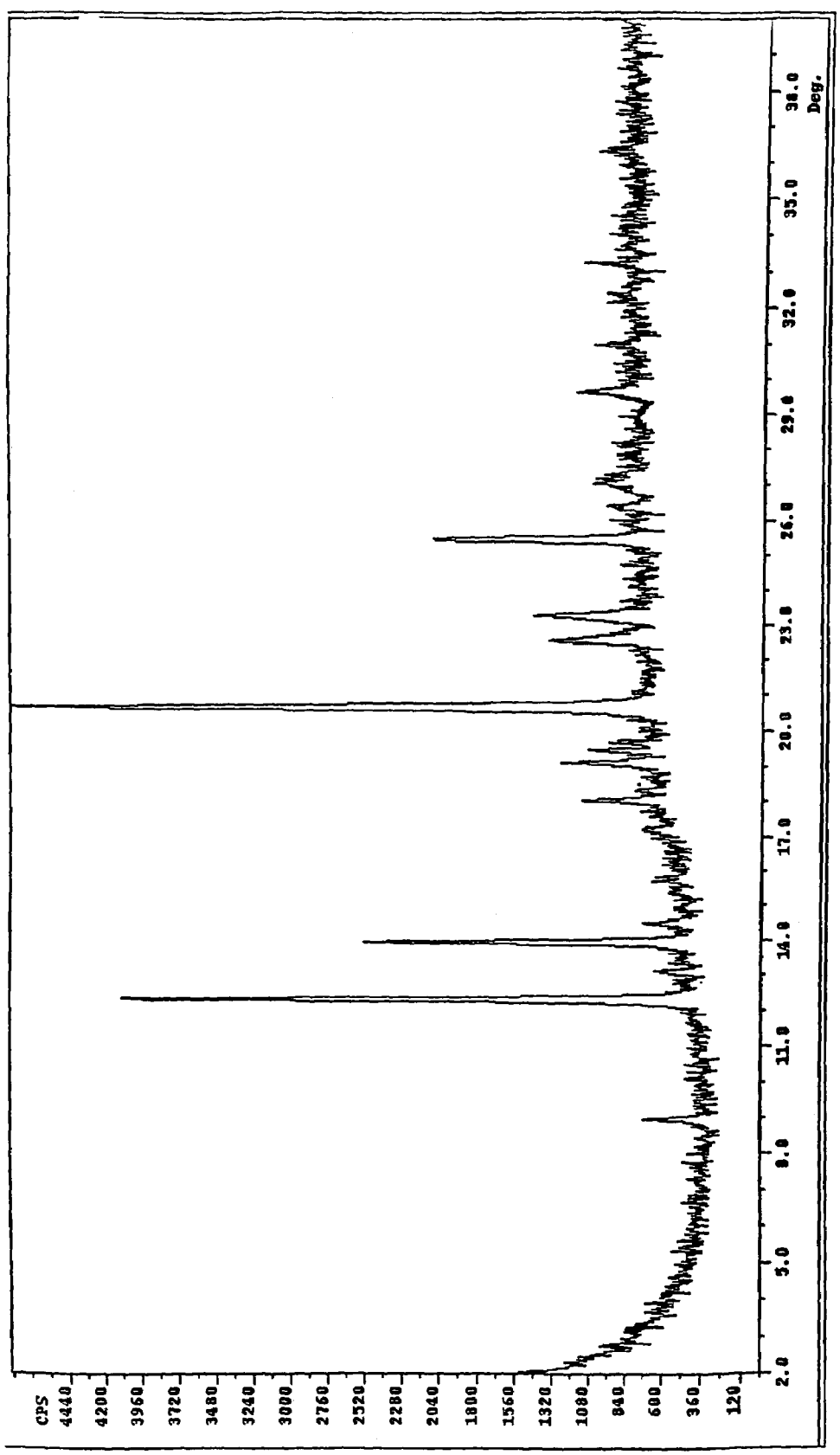
FIG. 11 is a PXRD pattern of a dehydrated form of racemic cis-FTC sesquihydrate.

Upon evaporating the waters of hydration from (±)-cis-FTC sesquihydrate, a dehydrated crystalline form of racemic cis-FTC is formed. The racemic cis-FTC thus obtained can be characterized by the powder diffraction pattern it exhibits when subjected to powder X-ray crystallography. The angular positions (two theta) of the characteristic peaks in the powder X-ray diffraction pattern of dehydrated racemic cis-FTC, shown in FIG. 11, are: 12.3°±0.1°, 14.0°±0.1°, 20.7°±0.1°, 22.6°±0.1°, 23.3°±0.1°, and 25.5°±0.1°. The dehydrated racemic cis-FTC has a melting temperature of about 190° C. at atmospheric pressure, and a heat of fusion of about 23 kJ/mol.

The DSC thermogram in FIG. 12 is (±)-cis-FTC sesquihydrate. As confirmed by TGA analysis, the large endotherm at about 80° C. was from (±)-cis-FTC sesquihydrate losing its water of hydration. The second endotherm at 190° C. is the melt of the dehydrated racemic cis-FTC.

Thus, in still another embodiment the invention provides the dehydrated (O)-cis-FTC of the present invention. In other embodiments the invention provides the dehydrated (+)-cis-FTC substantially in the absence of Form I (−)-cis-FTC, or substantially in the absence of other hydrated and dehydrated crystalline forms of racemic cis-FTC, (−)-cis-FTC, or (+)-cis-FTC. In still another embodiment the invention provides a pharmaceutical composition that comprises the dehydrated (±)-cis-FTC of the present invention, further comprising a pharmaceutically acceptable carrier.

Amorphous (−)-cis-FTC

Figure 15:
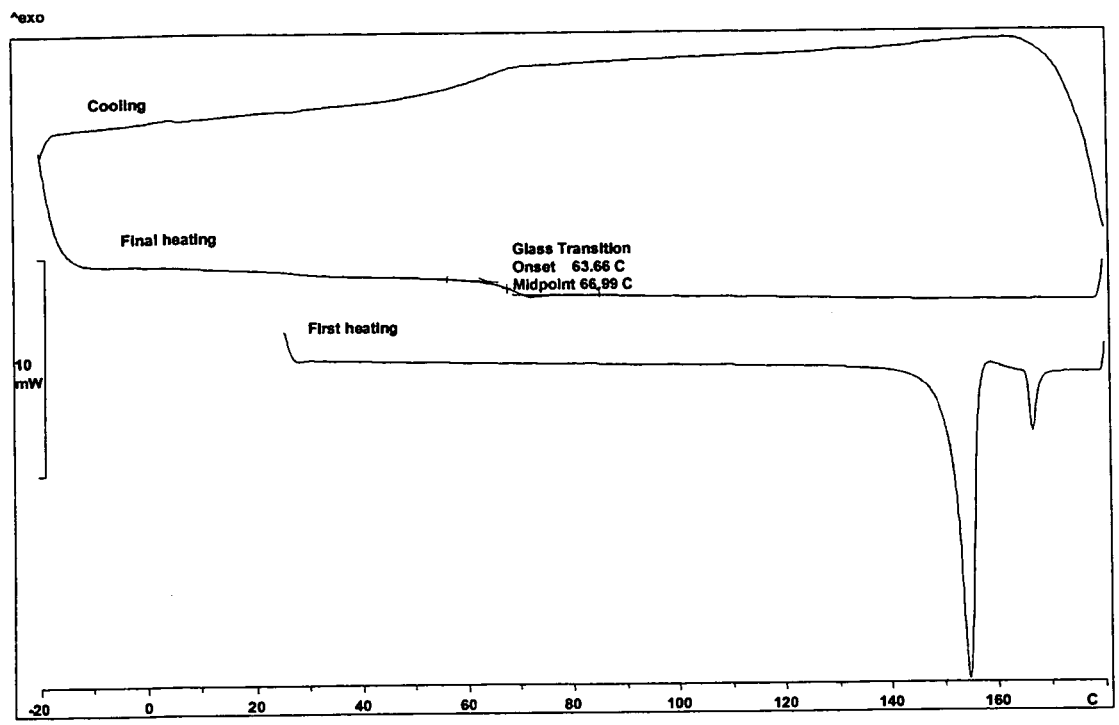
FIG. 15 is a DSC thermogram of amorphous (−)-cis-FTC obtained by melting and freezing a crystalline sample of (−)-cis-FTC. The final heating rate was 10° C./min.

An amorphous form of (−)-cis-FTC is obtained when melted (−)-cis-FTC is rapidly quenched to below about 40 or 50° C., thereby bypassing any transition to Forms II or III (−)-cis-FTC. A DSC thermogram of amorphous (−)-cis-FTC is presented as FIG. 15, which shows that the glass transition temperature for this phase is 67° C.

Therefore, in still another embodiment, the invention provides amorphous (−)-cis-FTC, preferably in substantially pure form. In another embodiment the invention provides amorphous (−)-cis-FTC substantially in the absence of Forms I, II, and/or III (−)-cis-FTC. In still another embodiment the invention provides a pharmaceutical composition that comprises amorphous (−)-cis-FTC, further comprising a pharmaceutically acceptable carrier.

Definitions

As used herein, the term, "substantially pure," when used in reference to a phase or crystalline form of FTC, refers to a phase or crystalline form of FTC which is greater than about 90% pure. This means that the polymorphic or hydrated form of FTC does not contain more than about 10% of any other compound and, in one embodiment, does not contain more than about 10% of any other phases or crystalline forms of FTC (whether racemic, (−), (+), cis, or trans). In other embodiments, the term "substantially pure" refers to a phase or crystalline form of FTC that is greater than about 95% pure. In still another embodiment the term "substantially pure" refers to a phase or crystalline form of FTC that is greater than about 97% or 99% pure.

Similarly, the term "substantially in the absence of a second component," when used in reference to a phase or crystalline form of FTC, refers to a phase or crystalline form of FTC that does not contain more than about 10% of the second component. More preferably, the term "substantially in the absence of a second component" refers to a phase or crystalline form of FTC that does not contain more than about 5% of the second component, and even more preferably no more than about 3% or 1% of the second component.

Characteristic power X-ray diffraction pattern peak positions are reported for crystalline forms in terms of the angular positions (two theta) within an allowable variability of plus or minus 0.1°. This allowable variability is specified by the US Pharmacopeia, pages 1843-1844 (1995). The variability of plus or minus 0.10 is intended to be used when comparing two powder X-ray diffraction patterns. In practice, if a diffraction pattern peak from one pattern is assigned a range of angular positions (two theta) which is a measured peak position plus or minus 0.1° and a diffraction pattern peak from the other pattern is assigned a range of angular positions (two theta) which is the measured peak position plus or minus 0.1° and if those ranges of peak positions overlap, then the two peaks are considered to have the same angular position (two theta). For example, if a diffraction pattern peak from one pattern is determined to have a peak position of 5.20°, for comparison purposes the allowable variability allows the peak to be assigned a position in the range of 5.10°-5.30°. If a comparison peak from the other diffraction pattern is determined to have a peak position of 5.35°, for comparison purposes the allowable variability allows the peak to be assigned a position in the range of 5.25°-5.45°. Because there is overlap between the two ranges of peak positions, the two peaks being compared are considered to have the same angular position (two theta).

Throughout this specification the word 'comprise,' or variations such as 'comprises' or 'comprising,' will be understood to imply the inclusion of a stated element, integer or step, or group of elements, integers or steps, but not the exclusion of any other element, integer or step, or group of elements, integers or steps.

EXAMPLES

Materials and Methods (−)-cis-FTC starting material for all tests, unless otherwise specified, was obtained by combining and treating two batches of (−)-cis-FTC as follows. A flask was charged with 1109 grams of (−)-cis-FTC and 2750-mL of ethyl acetate. This slurry was stirred at ambient temperature for two hours, filtered and washed with 550-mL of ethyl acetate. The filter cake was dried in a vacuum oven overnight at 50° C. and about 2-mm Hg. All solvents were HPLC grade and used as received. An HPLC assay of the starting (−)-cis-FTC indicated a purity of 98.8%.

Differential scanning calorimetry (DSC): The DSC experiments were conducted using one of the following instruments:

DSC studies were conducted using a TA Instruments DSC 2920 (with refrigerated cooling). Approximately 5-mg samples were placed in sealed aluminum pans. The DSC cell was purged with 30-mL/min nitrogen. The heating rate was 10° C./min unless otherwise noted. Temperature and heat flow calibrations were performed with an indium standard at the same experimental conditions.

DSC measurements were made in a Mettler DSC30, (Mettler Instrument, Hightstown, N.J.), equipped with a data analyzer (STAR$^e$, Mettler Instrument). The samples (ca. 2-5 mg) were sealed in standard 40 μL aluminum pans with a single hole punched in the lid. An empty pan of the sample type was used as a reference. The samples were scanned at 1-10° C./min with a 50 mL/min dry nitrogen purge. The DSC was calibrated for heat flow and temperature.

Thermogravimetric analysis (TGA): TGA studies were conducted with a TA Instruments TGA 2950. Approximately 5-mg samples were placed in open platinum pans and the sample was exposed to a heating rate of 10° C./min.

Variable-Temperature PXD: The diffractometer (XDS 2000, Scintag, Sunnyvale, Calif.) was comprised of a 4-kW generator (voltage 45 kV and current 40 mA) with a Cu anode tube, liquid nitrogen cooled Ge detector (GLP-101 95/07-S, EG&G ORTEC, Oak Ridge, TN), data analyzer (MicroVax 3100, Digital Equipment Corporation, Ontario, Canada), heating stage (Scintag) and temperature controller (Microstar, Research Inc., Minneapolis, Minn.). The samples were placed on the sample holder in a thin layer, and scanned at a rate of 1° per minute without spinning.

Hot-Stage Microscopy (HSM): Polarized light microscopy was performed using an Olympus BX60 microscope equipped with a Mettler-Toledo FP82HT hot stage. A thin layer of sample was placed on a slide and heated at 10° C./min. Thermal events were captured on ImagePro® software.

Recrystallization method: About 5 grams of (−)-cis-FTC were placed in a round-bottom flask and heated in the temperature range from 155 to 160° C. for 30 minutes with agitation. The sample was cooled in the flask to room temperature at ambient conditions.

Equilibrium Solubility: Equilibrium solubility values were obtained using an excess of solid in a stoppered flask shaken in a temperature-controlled water bath at 25° C. for 52 hours. Residual solid material was identified postequilibrium by hot-stage microscopy and PXRD. The supernatant was filtered across 0.45-μm membrane filters prior to dilution for HPLC analysis.

Milling: (−)-cis-FTC was milled in a Fitzpatrick mill at high speed (4000 RPM), hammers forward with a 000-band screen. The drug was passed through the filter once and collected in a plastic bag.

Hydrate Formation: A supersaturated solution (0.5 g/nL) of Form I was prepared at 50° C. This solution was then cooled to room temperature with stirring for a ca. 2 hours. The precipitated solid was vacuum filtered and air dried. This solid was analyzed by HPLC. DSC, PXRD and TGA. This analysis revealed that the solid was a sesquihydrate of (±)-cis-FTC.

Crystallization: (−)-cis-FTC was dissolved in one of the following solvents: methanol, ethyl acetate, water, tetrahydrofuran, and acetone. Each suspension was boiled for about 15 minutes and immediately filtered across a 0.45-μm nylon filter. The supernatant was stirred at room temperature until crystallization. At the point of crystallization, the suspensions were filtered to collect the filter cake. The filter cake was placed in a glass dish, covered with a lint-free paper towel and placed in a hood at ambient conditions for 2 days.

Example 1

DSC Characterization of (−)-cis-FTC Forms I and II

Thermal events of (−)-cis-FTC polymorph Form I were observed at heating rates of 10, 1, 2, and 5° C./min. These DSC thermograms are shown in FIGS. 1, 2, 3, and 4, respectively. Sample sizes were 6.8400 mg, 5.290 mg, 5.0430 mg, or 5.1500 mg, respectively.

The endotherm at 151° C. corresponds to the melt temperature of (−)-cis-FTC Form I. This endotherm was present at all heating rates studied. The heat of fusion associated with the melt of this phase is 25 kJ/mol. This melting is followed by recrystallization to a higher melting solid, Form II. The presence of the high-temperature endotherm (162° C.) was dependent on the heating rate. Specifically, as the heating rate decreased, the probability increased that the high-temperature endotherm would appear. Also, the heat of fusion value increased for the high-temperature endotherm as the heating rate decreased. These observations are consistent with the fact that at slower heating rates the liquid recrystallizes to a greater extent. This heating-rate-dependent endotherm indicated that Form I may undergo recrystallization after melting at 151° C., and that the resulting crystal form melts at about 162° C. The phase that melts at 162° C. was designated "(−)-cis-FTC Form II."

Example 2

DSC Characterization of (−)-cis-FTC Forms II and III

Figure 1:
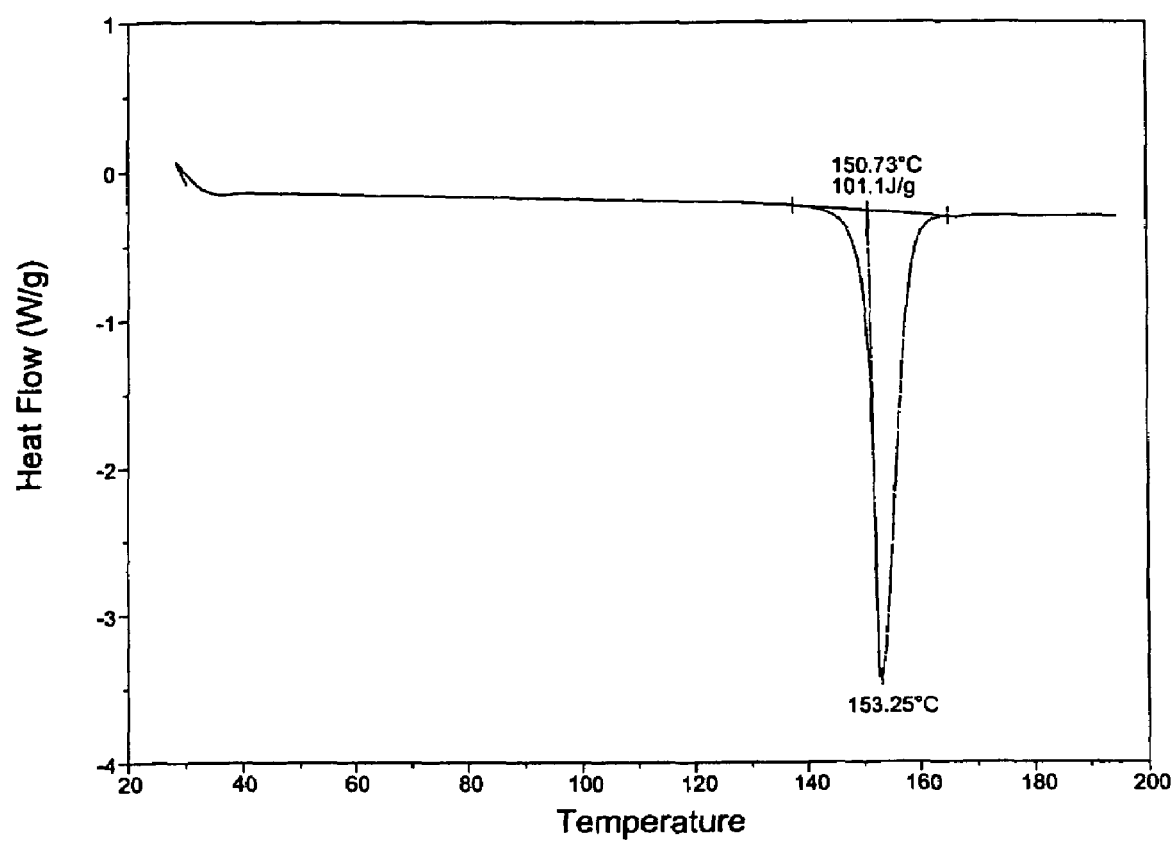
FIG. 1 is a typical DSC ("differential scanning calorimetry") thermogram of (−)-cis-FTC Form I, with an endotherm at 151° C., obtained by heating at a rate of 10 IC/min.
Figure 2:
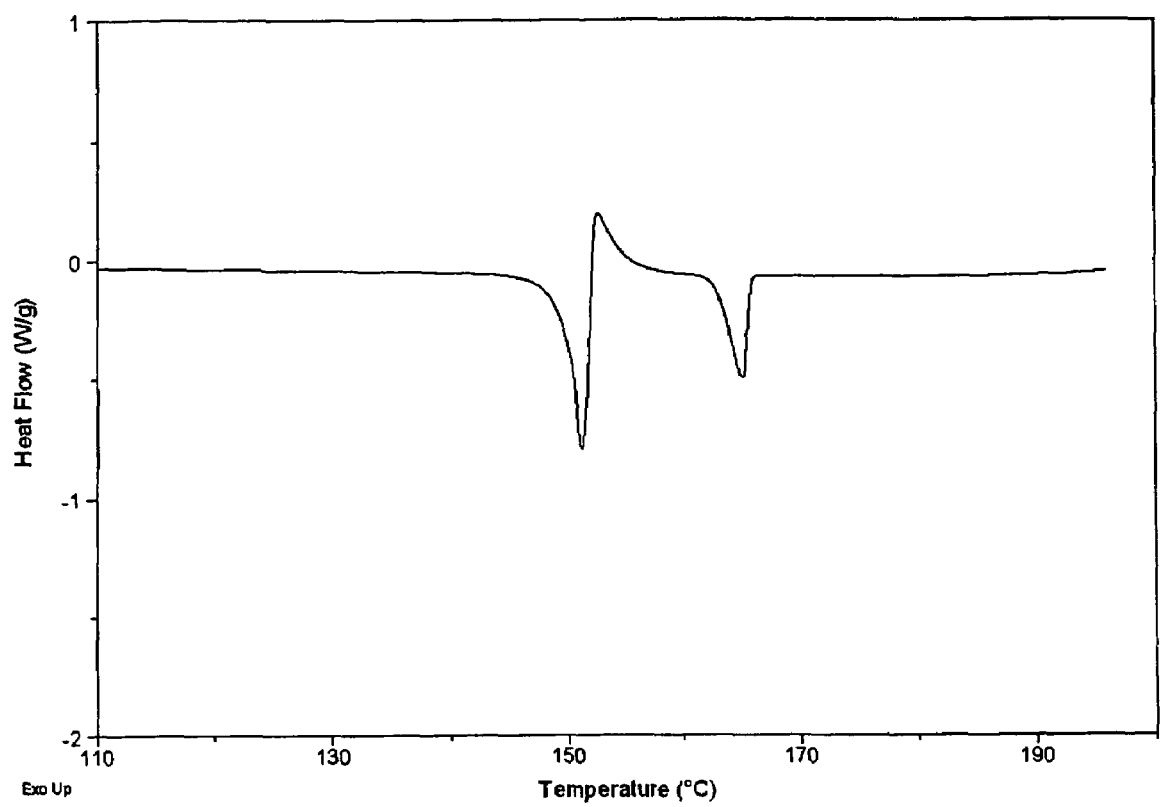
FIG. 2 is a DSC thermogram of (−)-cis-FTC Form I obtained by heating at 1° C./min.
Figure 3:
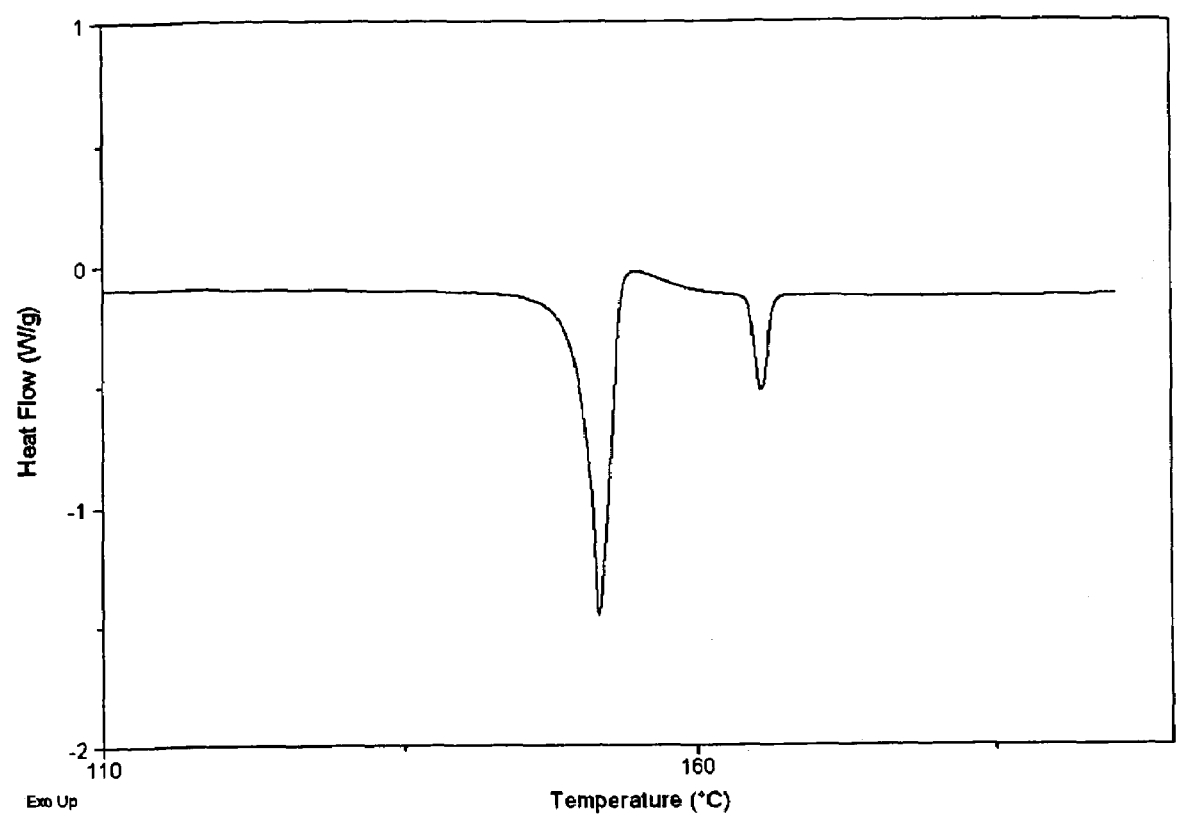
FIG. 3 is a DSC thermogram of (−)-cis-FTC Form I obtained by heating at 2° C./min.
Figure 4:
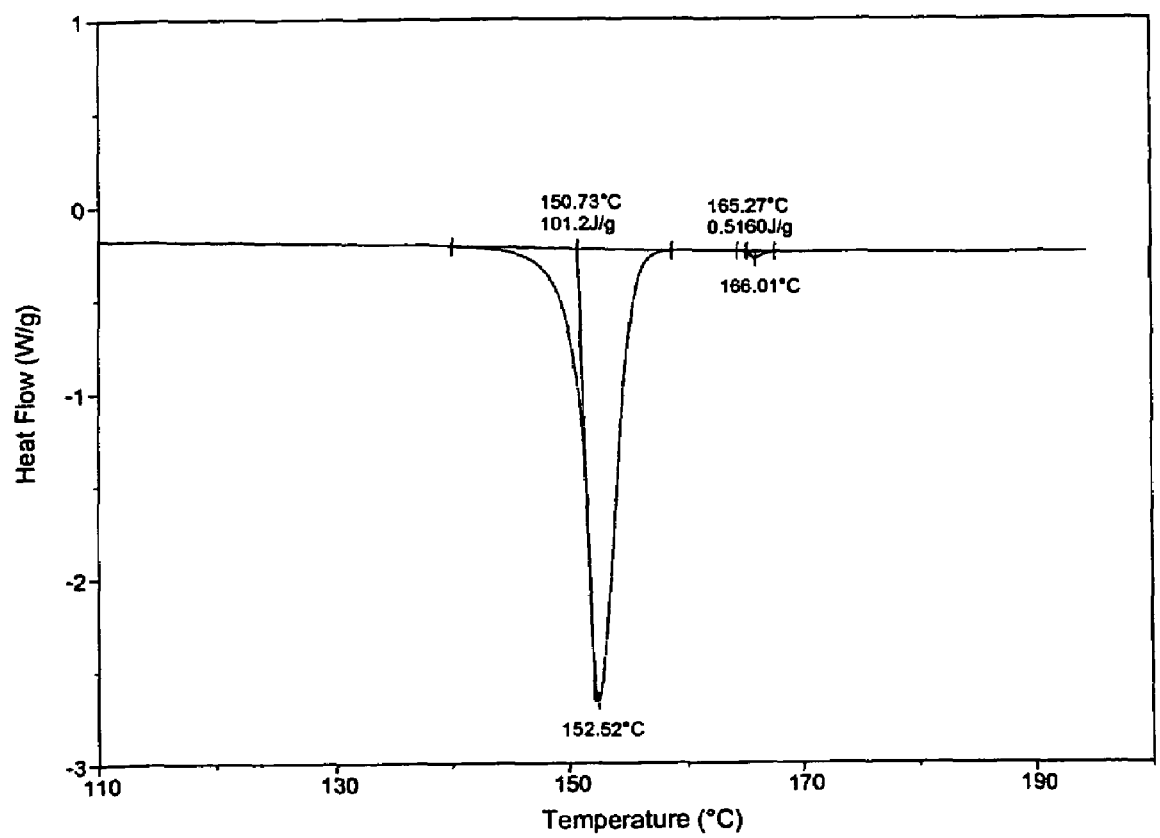
FIG. 4 is a DSC thermogram of (−)-cis-FTC Form I obtained by heating at 5° C./min.
Figure 5:
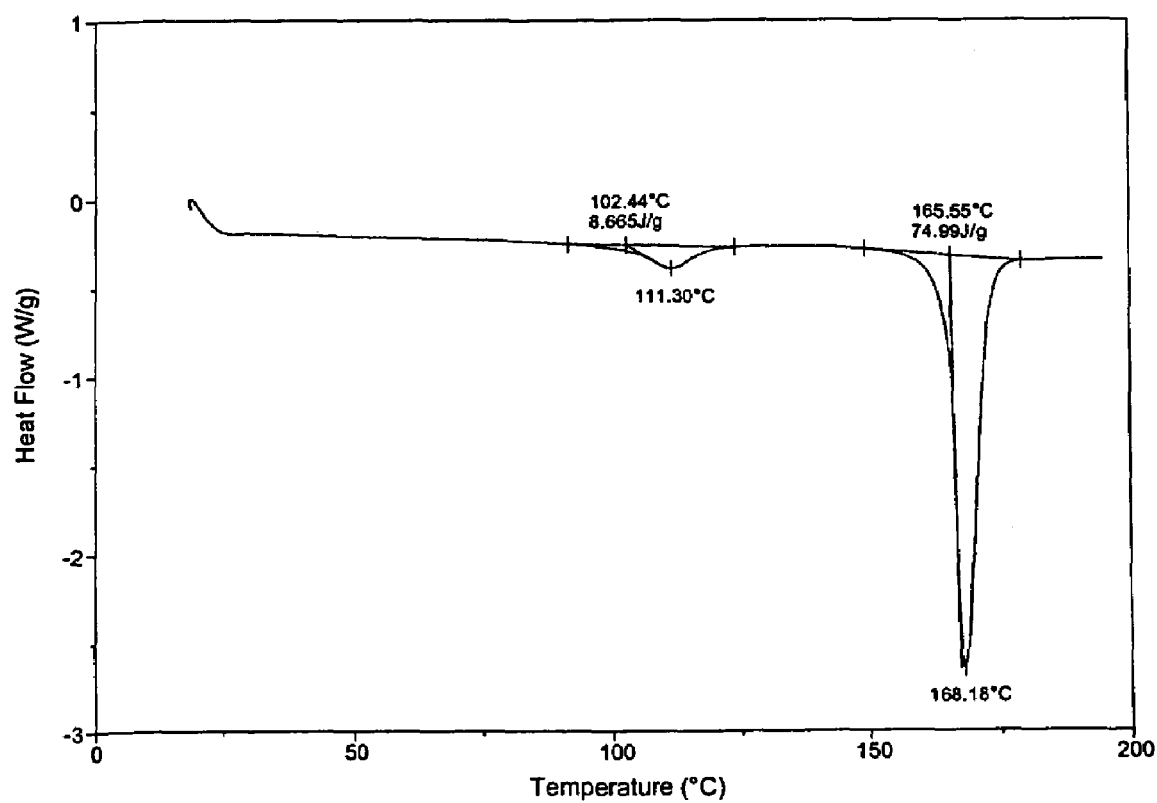
FIG. 5 is a DSC thermogram of Form II and III (−)-cis-FTC.
Figure 6:
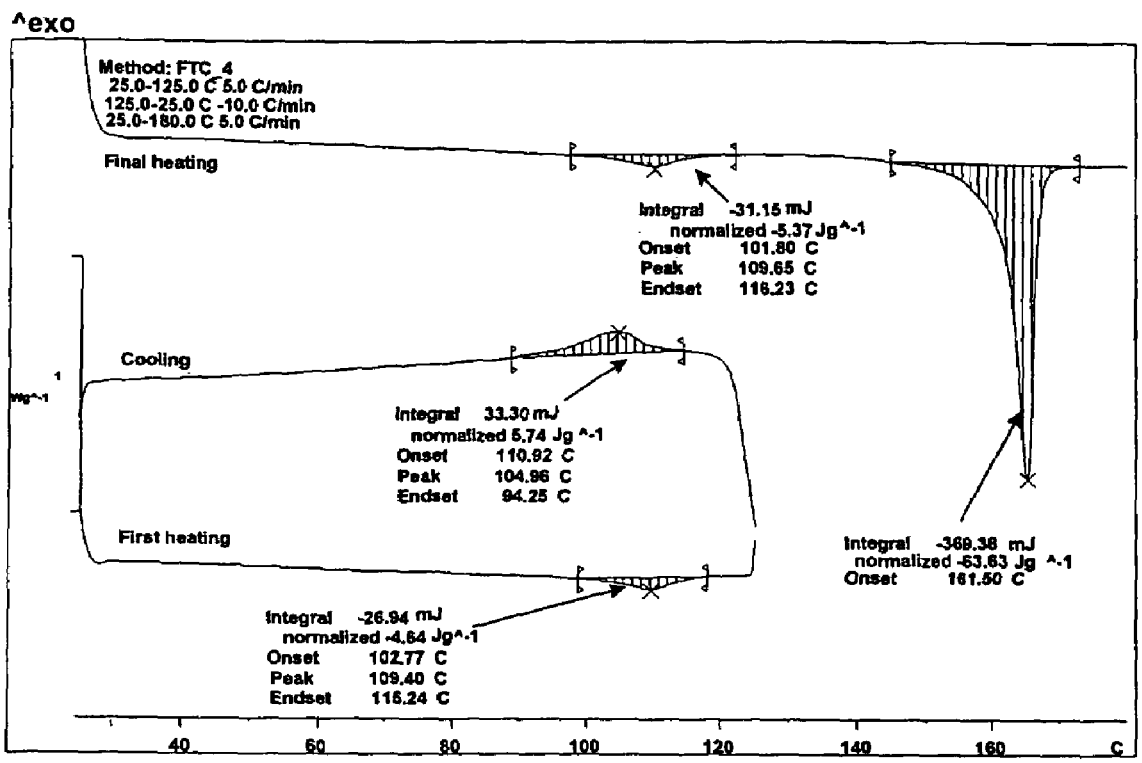
FIG. 6 is a DSC thermogram showing that the Form II to III transition is reversible.

Thermal events for Form I (−)-cis-FTC upon melting and subsequent cooling to room temperature were observed by DSC. A 5.5500 mg sample of Form I (−)-cis-FTC was heated to 160° C., that is just above the melting temperature for Form I, and then cooled back to 25° C. When reheated in the DSC using a heating rate of 10° C./min, the endotherm at 151° C. for Form I (−)-cis-FTC was not present. However, endotherms did appear at 102° C. and 162° C., as shown in FIG. 5. The endotherm at 102° C. was a solid state transition of Form In (−)-cis-FTC to Form II (−)-cis-FTC as shown in FIG. 6. The PXRD data (FIGS. 7 and 9) collected above and below the 102° C. transition confirmed the DSC interpretation. The endotherm at 162° C. was the melt of Form II (−)-cis-FTC. HPLC confirmed that there was no change in potency associated with these thermal events.

Example 3

DSC Characterization of Amorphous (−)-cis-FTC

A 7.315 mg of Form I FTC was heated to 180° C. at 5° C./min in the DSC. Then the sample was quench cooled at −20° C./min to −20° C. This sample when re-heated at 10° C./min showed a shift in baseline associated with glass transition at ~67° C. This shift in baseline occurred during both the heating and cooling cycle confirming that it was due to glass transition. A DSC thermogram of the amorphous (−)-cis-FTC is contained in FIG. 15.

Example 4

HSM Observations of Forms I, II, and III (−)-cis-FTC

The assignment of Forms I, II and III based upon thermal events observed during DSC analysis was consistent with HSM observations. Under the microscope, Form I material appeared as plates at room temperature. Upon heating to 160° C. at 10° C./min, Form I melted to a clear liquid. On cooling this liquid, acicular needles crystallized from the melt, which were darker in appearance compared to Form I. On reheating, these needles underwent a change in birefringence beginning at about 102° C. and ending at about 115° C. The needles eventually melted at 166° C.

Example 5

Effect of Milling on Crystal Form

Two batches of milled Form I (−)-cis-FTC were prepared: one by hand trituration in a mortar and pestle for 5 minutes, another by milling in a Fitzpatrick mill. Although not quantitatively measured, light microscopy revealed that the particle size of triturated (−)-cis-FTC appeared smallest followed by that obtained using the Fitzpatrick mill and then unmilled (−)-cis-FTC. The DSC thermogram of sample milled by Fitzpatrick mill and unmilled (−)-cis-FTC had only one endotherm at 151° C. Triturated (−)-cis-FTC had two endotherms at 151° C. and 162° C. The PXRD pattern of the triturated (−)-cis-FTC at room temperature was the same as the pattern for Form I, which indicated that conversion from Form I to II occurred during the DSC experiment. Taken together, these data indicate that milling according to the described conditions does not affect the crystal form of (−)-cis-FTC when starting with Form I.

Example 6

Effect of Heat on Crystal Form

The PXRD pattern for Form III at 25° C. and 95° C., is shown in FIG. 9. However, a PXRD pattern of this sample acquired at 120° C. was different from the pattern acquired at 95° C. The PXRD pattern change over this temperature range was consistent with the endotherm obtained at about 102° C. by DSC thermogram analysis (FIG. 6), and confirms that the 102° C. endotherm was caused by a solid-state transition or change in crystal structure.

The PXRD pattern measured at 120° C. was the same as that measured at 160° C. However, upon cooling the sample back to 25° C., the PXRD pattern was the same as Form III (−)-cis-FTC. The crystal form that exists above 102° C. and melts at 162° C. was identified as Form II. The PXRD pattern for Form I material did not change up to the melting temperature of 151° C.

Example 7

Thermodynamic Stability Analysis

The melting data for Forms I, II, and III, (−)-cis-FTC, are summarized in Table I. Based on this data the thermodynamic relationship between Forms I and II was established. These forms are enantiotropically related and the calculated transition temperature is 130° C.

TABLE I

Transition temperature data for four crystalline forms of (−)-cis-FTC.

| Form | Transition Temperature (° C.) | Heat of Fusion (kJ/mol) |
| --- | --- | --- |
| I | 151 | 25 |
| II | 166 | 18 |
| III* | 102 | — |
| Racemic cis-FTC | 186 | 22.8 |

*Form III does not undergo melting but rather a solid-state transition at about 112° C., therefore heat of fusion is not known.

Figure 14:
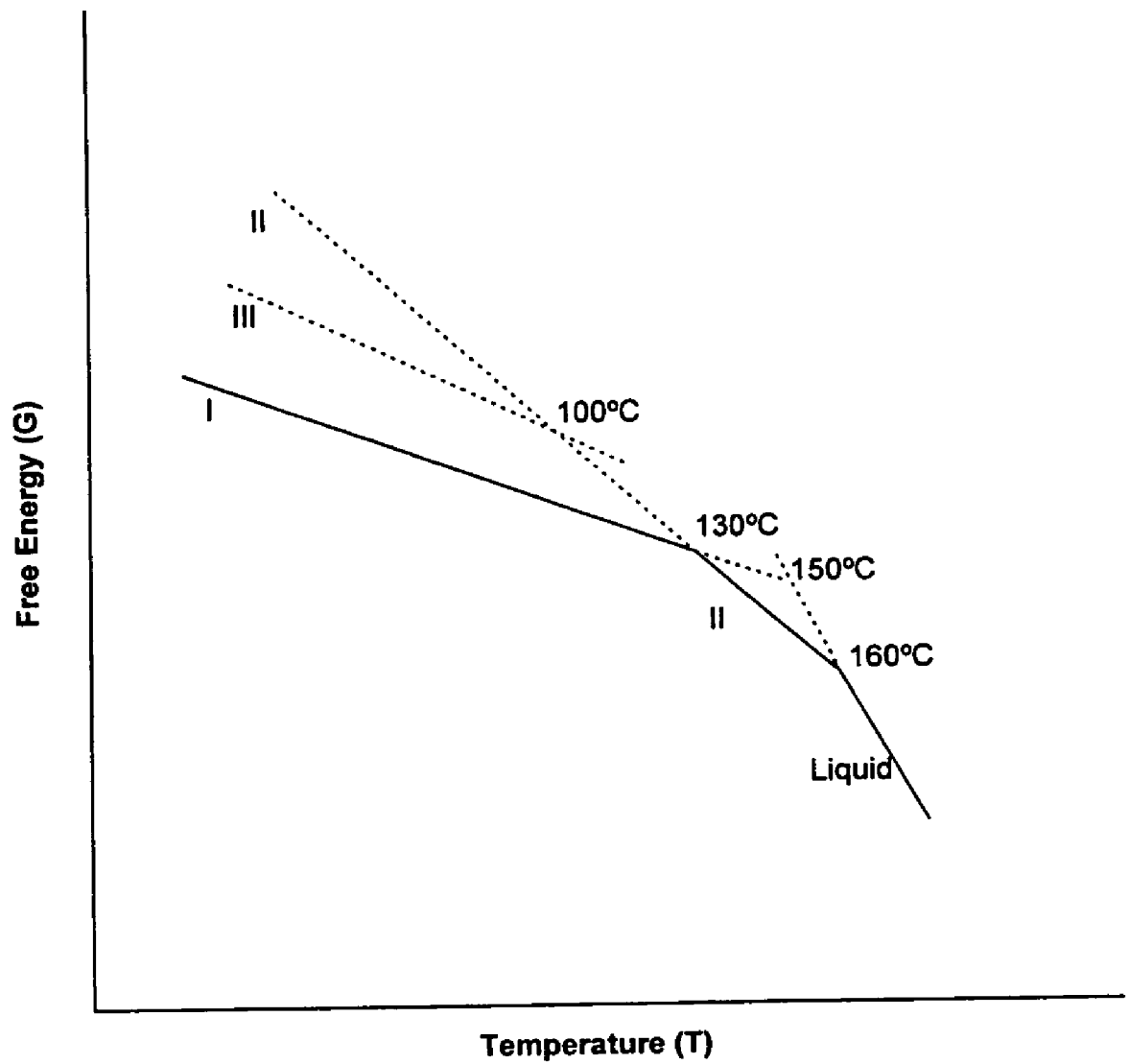
FIG. 14 is a free energy-temperature relationship for three polymorphs of (−)-(cis)-FTC (Forms I, II, and III). The stable phases are represented by a solid line and the metastable phases by a dotted line.

The thermodynamic stability relationship between these forms are graphically depicted in FIG. 14.

Example 8

Solubility

It is evident from FIG. 14 that below 130° C., Form I is the most stable phase. Therefore, below 130° C., Form I is the least soluble phase. The equilibrium solubility for Form I in water at 25° C. was 0.482 M (119 mg/mL). Compounds having solubility values greater than 100 mg/mL are considered highly soluble and (−)-cis-FTC Form I falls in this category. The other forms of (−)-cis FTC described here would have solubility greater that Form I.

Example 9

Crystallization Studies

The (−)-cis-FTC starting material for all crystallization studies was Form I (−)-cis-FTC as determined by PXRD. Form I (−)-cis-FTC was recrystallized from solutions of water, methanol, tetrahydrofuran, ethyl acetate, and acetone. All samples from the crystallization experiments were analyzed by PXRD and DSC. (−)-cis-FTC crystallized from ethyl acetate and acetone exhibited endotherms at 151° C. and 162° C., and PXRD patterns identical to the pattern for Form I (−)-cis-FTC.

Figure 13:
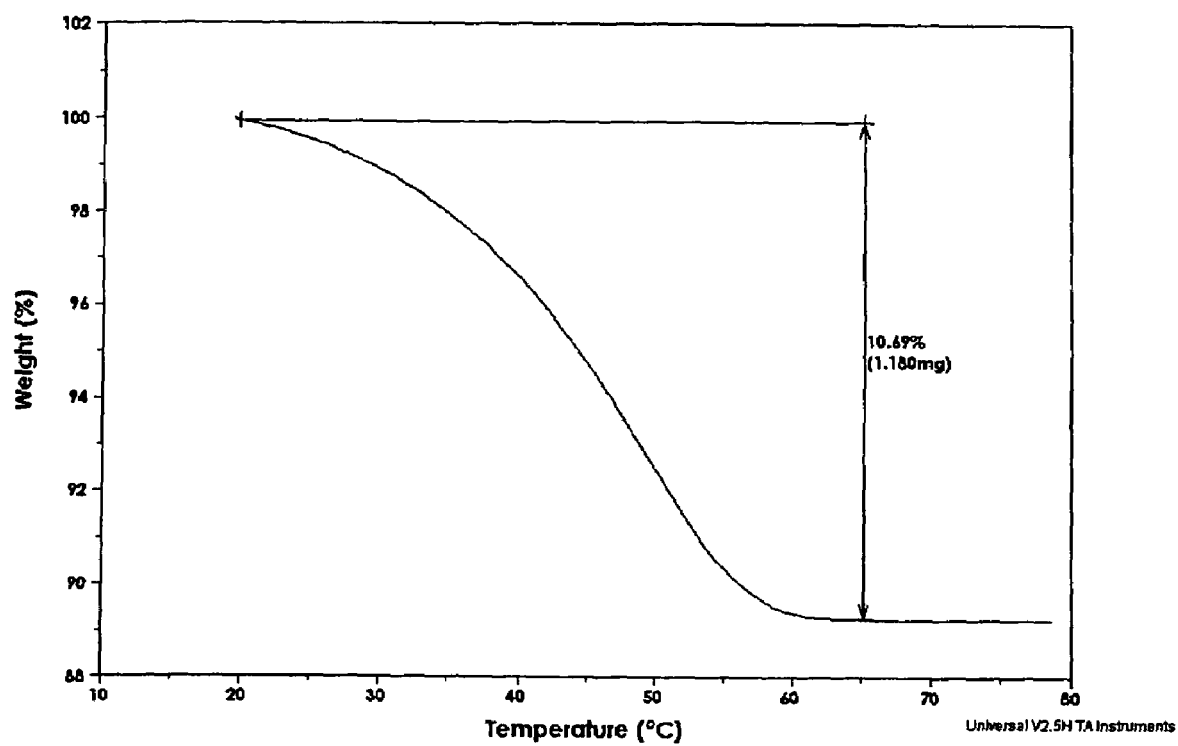
FIG. 13 is a TGA ("thermogravimetric analysis") scan of the sesquihydrate of (+)-cis-FTC.

A supersaturated solution (0.5 g/mL) of Form I was prepared at 50° C. This solution was then cooled to room temperature with stirring for a ca. 2 hours. The precipitated solid was vacuum filtered and air dried. This solid was analyzed by HPLC. DSC, PXRD and TGA. This analysis revealed that the solid was a sesquihydrate of (±)-cis-FTC. The equilibrium solubility of the sesquihydrate at 25° C. is 0.34 M (93 mg/mL). The DSC thermogram of the hydrate is shown in FIG. 12. The large endotherm at low temperatures was due to loss of water of hydration from (±)-cis-FTC sesquihydrate, which was confirmed by TGA (FIG. 13). The endotherm at 190° C. was due to the melt of the dehydrated hydrate. The dehydrated hydrate was subsequently assigned a unique melting temperature of about 190° C., FIG. 12. A unique PXRD pattern was also collected for the dehydrated hydrate. (See FIG. 11)

Pharmaceutical Compositions

Humans suffering from HIV and HBV can be treated by administering to the patient an effective amount of the various compounds of the present invention (i.e. Forms II and III (−)-cis FTC, racemic cis-FTC sesquihydrate, and the dehydrated form of racemic cis-FTC sesquihydrate) or a pharmaceutically acceptable prodrug or salt thereof in the presence of a pharmaceutically acceptable carrier or diluent. The active materials can be administered by any appropriate route, for example, orally, parenterally, or intravenously, in liquid or solid form.

A preferred dose of the compound for HIV or HBV will be in the range from about 1 to 75 mg/kg, preferably 1 to 50 or 20 mg/kg, of body weight per day, more generally 0.1 to about 100 mg per kilogram body weight of the recipient per day. The effective dosage range of the pharmaceutically acceptable salts and prodrugs can be calculated based on the weight of the parent nucleoside to be delivered. If the salt or prodrug exhibits activity in itself, the effective dosage can be estimated as above using the weight of the salt or prodrug, or by other means known to those skilled in the art.

The compound is conveniently administered in unit any suitable dosage form, including but not limited to one containing 7 to 3000 mg, preferably 70 to 1400 mg of active ingredient per unit dosage form. An oral dosage of 50-1000 mg is usually convenient.

Ideally the active ingredient should be administered to achieve peak plasma concentrations of the active compound of from about 0.2 to 70 μM, preferably about 1.0 to 10 μM. This may be achieved, for example, by the intravenous injection of a 0.1 to 5% solution of the active ingredient, optionally in saline, or administered as a bolus of the active ingredient.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound can be administered as a component of an elixir, suspension, syrup, wafer, chewing gum or the like. A syrup may contain, in addition to the active compounds, sucrose as a sweetening agent and certain preservatives, dyes and colorings and flavors.

The compound or a pharmaceutically acceptable prodrug or salts thereof can also be mixed with other active materials that do not impair the desired action, or with materials that supplement the desired action, such as antibiotics, antifungals, anti-inflammatories, or other antivirals, including other nucleoside compounds. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation.

Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A dehydrated crystalline form of (±)-cis-FTC prepared by a method comprising:
   a. dissolving a first crystalline form of (±)-cis-FTC in water;
   b. recrystallizing the dissolved (±)-cis-FTC; and
   c. dehydrating the recrystallized (±)-cis-FTC;
   wherein the dehydrated crystalline form of (±)-cis-FTC is substantially in the absence of Form I (−)-cis-FTC or substantially in the absence of hydrated crystalline (±)-cis-FTC.

2. A pharmaceutical composition comprising a therapeutically effective amount of the crystalline form of (±)-cis-FTC of claim 1 in combination with a pharmaceutically acceptable carrier.

3. The pharmaceutical composition of claim 2, wherein the carrier is suitable for oral delivery.

4. The pharmaceutical composition of claim 2, wherein the composition is in the form of a dosage unit.

5. The pharmaceutical composition of claim 3, wherein the (±)-cis-FTC is present in an amount from 70-1400 mg.

6. The pharmaceutical composition of claim 3, wherein the (±)-cis-FTC is present in an amount from 50-1000 mg.

7. The pharmaceutical composition of claim 2, wherein the composition is in the form of a tablet.

8. The pharmaceutical composition of claim 2, wherein the composition is in the form of a pill.

9. The pharmaceutical composition of claim 2, wherein the composition is in the form of a capsule.

* * * * *